United States Patent [19]

Goodman

[11] Patent Number: 4,894,728
[45] Date of Patent: Jan. 16, 1990

[54] DATA ACQUISITION AND RECORDING SYSTEM

[76] Inventor: Robert M. Goodman, 7811 Mill Rd., Elkins Park, Pa. 19117

[21] Appl. No.: 288,794
[22] PCT Filed: Jun. 27, 1986
[86] PCT No.: PCT/US86/01385
 § 371 Date: Oct. 12, 1988
 § 102(e) Date: Oct. 12, 1988
[87] PCT Pub. No.: WO88/00384
 PCT Pub. Date: Jan. 14, 1988

Related U.S. Application Data

[63] Continuation-in-part of Ser. No. 706,022, Feb. 27, 1985, abandoned.

[51] Int. Cl.⁴ .......................... G11B 5/00; G11B 5/09
[52] U.S. Cl. ........................................ 360/6; 360/52
[58] Field of Search .................. 360/6, 52, 15, 45, 32

[56] References Cited

U.S. PATENT DOCUMENTS

| 3,319,237 | 5/1967 | Jones, Jr. | 360/51 |
| 3,512,146 | 5/1970 | Smith et al. | 340/174.1 |
| 3,889,294 | 6/1975 | Anderson et al. | 360/52 |
| 3,995,313 | 11/1976 | Fayling | 360/15 |
| 4,183,354 | 1/1980 | Sibley et al. | 128/711 |
| 4,211,238 | 7/1980 | Shu et al. | 128/700 |
| 4,216,462 | 8/1980 | McGrath et al. | 340/150 |
| 4,216,779 | 8/1980 | Squires et al. | 360/6 |
| 4,333,475 | 6/1982 | Moreno et al. | 128/711 |
| 4,483,346 | 11/1984 | Slavin | 128/710 |
| 4,519,011 | 5/1985 | Bowden | 360/6 |
| 4,553,178 | 11/1985 | Lynch | 360/45 |

OTHER PUBLICATIONS

"CMOS Data Logger Records with 900 mW, idles on 10 Mw", Electronic Design, p. 90, 3-15-73.

Primary Examiner—Vincent P. Canney
Attorney, Agent, or Firm—Dann, Dorfman, Herrell and Skillman

[57] ABSTRACT

A portable, self-contained data acquisition and recording system is provided for monitoring ambulatory subjects. The system has micropower requirements and an extended recording capability between battery replacements. A prepolarized magnetic tape is employed and recording is accomplished by selectively reversing the polarization at a time when the tape is at rest. A microprocessor is provided for processing signals and for controlling circuit operation such as a tape drive incrementer. The microprocessor also controls the preprocessing and digitizing of signals for further processing by the microprocessor and enables the delivery of digital signals to be recorded to a magnetic tape head positioned in operative relationship with the magnetic tape. Selected circuits of the system are selectively powered up and powered down during monitoring as needed to provide continuous power control for optimization of power usage.

26 Claims, 3 Drawing Sheets

DATA ACQUISITION AND RECORDING SYSTEM

This application is a continuation-in-part of U.S. patent application Ser. No. 706,022, filed Feb. 27, 1985 (now abandoned).

FIELD OF THE INVENTION

The present invention relates to a data acquisition and recording system and more particularly to a portable monitoring system which can be carried on ambulatory subjects for extended periods of time.

BACKGROUND OF THE INVENTION

Systems for acquisition and/or recording data by telemetry have been known and used for many years. Such systems employ an electronic device to sense and measure preselected conditions and to then transmit the information thus obtained to a remote receiver or receivers where the information is recorded and further processed. While there are data acquisition cases where such telemetry systems may be used, there are many other cases where telemetry systems do not operate satisfactorily. This is particularly true in the case of accumulating a mix of biological and/or clinical data from free roaming subjects over relatively long periods of time, for example weeks, months or even years. Typical examples of critical applications are chronobiological data; pre-stress, stress and post-stress data in sequence; long-term isolation data; drug studies; and specific categories of clinical data for chronic periods.

Telemetry does not provide a satisfactory solution for any of the above cases. A free-roaming subject presents significant technical problems for telemetry, particularly in urban environments and in those cases in which the subject moves through substantially different environments in normal movement. The transmission of data through such changing environments may adversely affect the data being transmitted. Moreover, the transmittor frequently requires significant power input which in turn adds significantly to the weight of the system.

Although portable systems have also been developed, a significant problem is that power consumption in the conventional systems is not effectively optimized. The lack of adequate power control in conventional systems greatly restricts the period of time that the system can be used without requiring a replacement battery.

In accordance with the present invention, a data acquisition and recording system is provided which is particularly useful in acquiring and recording biological and/or clinical data over long periods of time from free-roaming, ambulatory subjects. More particularly, the present invention provides a self-contained system for acquiring and recording data which can be worn unobtrusively by the subject under observation for long periods of time and which is capable of accumulating and storing, in a nonvolatile form, extremely large quantities of several classes of data.

The system, including its power supply, is sufficiently small so as not to interfere with the subject's normal activities and is relatively light in weight. Moreover, power usage is specifically controlled so that the system requires extremely low power for its intended operation, and therefore, can be used for long periods of time. For example, various circuits of the system are powered up and powered down as needed continuously during the monitoring process to provide almost continual power control for the optimization of power usage.

One of the problems faced by the worker in the field of chronobiology relates to the acquisition of smooth-profile data for periods substantially in excess of several weeks. Further, it is sometimes necessary to acquire data which includes a number of different parameters such as heart rate, ectopic heart beat, body temperatures, sweat ion-level concentration and other related parameters.

In the clinical and bio-research situation it has become a matter of considerable importance to establish circadian patterns for human and animal subjects. Circadian patterns are expected to be useful in analyses related to the onset of episodic mental problems, the establishment of optimal times for radiation treatment and/or chemotherapy and the selection of crew members for shared-crew missions.

In stress-related studies, the system in accordance with the present invention makes it possible to follow subjects during a pre-stress period, the stress period and post-stress period. Examples may include subjects participating in spaceflight where they would be observed from well before the flight, during lift-off, orbit, reentry, touchdown and for substantial post-flight periods. Special mission members or crews may be studied during pre-mission, mission and post-mission time periods. The air-traffic controller represents another subject for continuous stress/nonstress data acquisition. Controllers can easily be studied continuously on and away from the job through use of the system in accordance with the present invention. Long-term "isolation" data could also be acquired from nuclear submarine crew members and from subjects located for long periods at remote inclement sites, as in exploration missions, both terrestrial and in space. It would be possible to acquire data from scuba divers including related physical parameters of depth, water temperature, pressure and the like. Certainly for undersea habitat research, smooth profile, long-term data acquisition would be possible and would be of great interest.

Subjects used for drug studies are of interest with regard to the collection of heart rate and body temperature data, both during prestudy and over the course of the study. Using such data and other parameters of interest may be of further use to aid in the establishment of optimum time of administration, within the circadian period, of drugs for enhanced efficacy, for reduction of undesirable side-effects and for reduced dosage levels.

From a clinical viewpoint, the patient subject to a periodic arrhythmia is of major interest. Such patients could be followed for extended time periods and the occurrence of arrhythmias adequately recorded including the previous normal ECG-complex, the R—R spacings in milliseconds, the ectopic complex, time of occurrence and other related types of information.

SUMMARY OF THE INVENTION

The present invention relates to a portable data acquisition and recording system which is capable of being carried on an ambulatory subject for monitoring selected conditions of the subject over an extended time period. The data acquisition and recording system incorporates a recording tape, such as a microcassette, and a power supply, such as a battery.

The system includes a sensor circuit in communication with the subject for sensing at least one selected parameter of the subject, such as heart rate or temperature, and for producing signals representing the parameter being sensed. Interface circuitry is connected with the sensor circuit for converting signals originating at the sensor circuit into digital signals of a selected format. In specific applications, the interface circuit may include a signal preprocessing circuit connected with the sensor circuit for modifying the signals originating at the sensor circuit into a predetermined form. The interface circuit may also include an analog-to-digital converter circuit connected with the signal preprocessing circuit for converting analog signals from the signal preprocessing circuit into digital signals of a selected format.

A recording head is provided for recording digital signals on the recording tape in a limited area adjacent the recording head preferably while the tape is at rest. In a specific application, the system may include a circuit for prepolarizing the recording tape so that the recording head records digital signals by intermittently reversing the polarization of the prepolarized recording tape. An incremental tape drive circuit is provided for incrementally advancing the tape to permit recording of successive digital signals while the tape is at rest between incremental advances.

A microprocessor controls circuit operation, processes signals and enables digital signals which are to be recorded to be supplied to the tape head while the tape is at rest. A memory circuit is associated with the microprocessor for storing information. In specific applications, the memory circuit may include an integral memory of the microprocessor or an external memory in the form of a buffer circuit or RAM memory.

Power control means, including, for example, program circuitry, such as a ROM, is associated with the processor for continually optimizing power usage of the system during subject monitoring. The power control means selectively prevents power from being respectively supplied to any selected circuit of the system at those time periods during monitoring when any such selected circuit is not required to perform functions requiring power usage. The power control means also enables power to be respectively supplied to any selected circuit of the system only at those respective time periods during monitoring when any such circuit is required to perform a desired function requiring power usage and then only for the general time period required for any such circuit to perform the desired function.

BRIEF DESCRIPTION OF THE DRAWINGS

The foregoing summary as well as the following detailed description of a preferred embodiment of the present invention, will be better understood when read in conjunction with the accompanying drawings, in which.

DETAILED DESCRIPTION OF THE INVENTION

Figure 5:
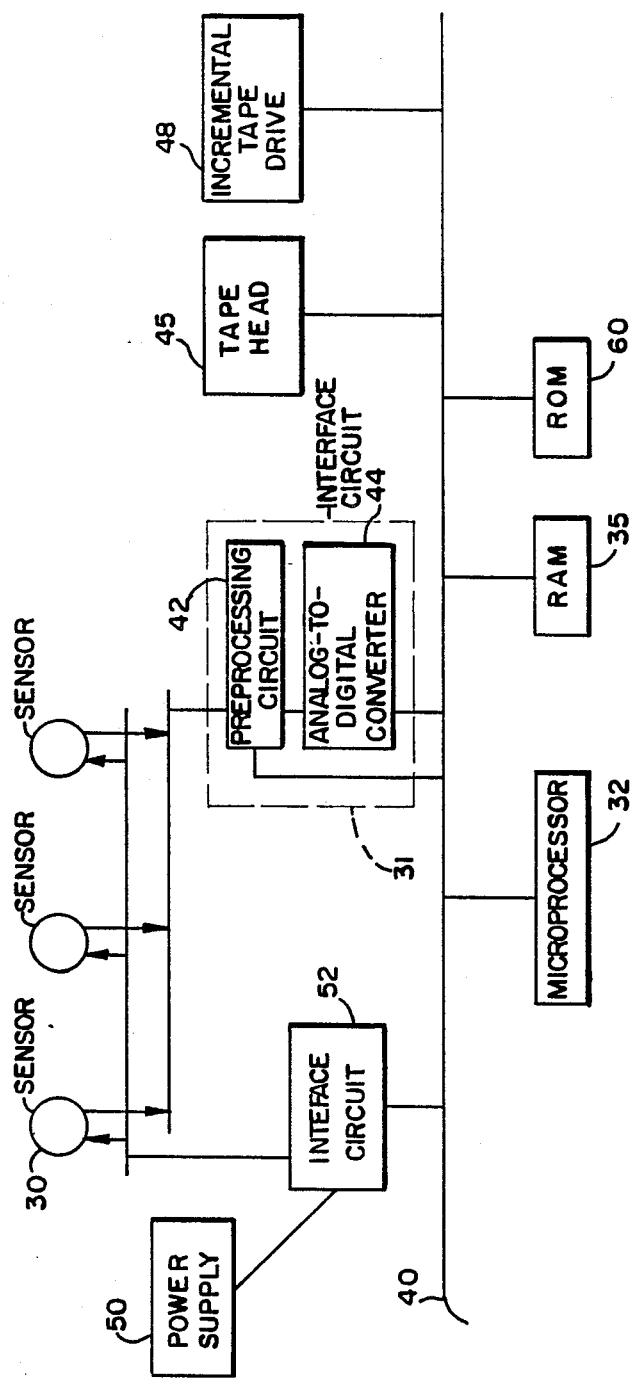
FIG. 5 is a generalized functional block diagram showing the processing elements of the present invention.

As shown in FIG. 5, a plurality of sensors 30 are depicted for application to an ambulatory subject for the purpose of communicating with the subject to sense at least one selected parameter, such as heart rate or temperature, of the subject. The sensors 30 produce an analog signal representing the parameter being sensed and supply the signal to a suitable interface circuit 31 connected with the sensors 30. The interface circuit 31 normalizes and converts the signals originating at the sensors 30 into digital signals of a selected format. The digital signal from the interface circuitry 31 is supplied to a suitable bus system 40 under the control of microprocessor 32. The bus system 40 includes the respective data, control, and address buses essential for operation of the system and further includes the necessary power supply lines operating under the control of the microprocessor.

Depending on the parameters being sensed by sensors 30, the interface circuit 31 may include a signal preprocessing circuit 42 connected with the sensors 30 for modifying the signals originating at the sensor circuit to a suitable format. For example, the preprocessing circuit may normalize and convert the analog signal from the sensor 30 to a desired digital format for direct output onto bus 40. In other applications, where different parameters are sensed by the sensors 30, preprocessing circuit may simply modify the analog signal originating at the sensor circuit to an acceptable format for input to an analog-to-digital converter circuit 44. The analog-to-digital converter is connected with the signal preprocessing circuit and functions to convert the analog signals from the preprocessing circuit into digital signals of a suitable format for output onto bus 40.

A recording head 45 and suitable interface circuitry is provided for recording digital signals on recording tape in a limited area adjacent the recording head while the recording tape is at rest. An incremental tape drive circuit 48 operates under the control of the microprocessor for incrementally advancing the recording tape to permit the recording of successive digital signals while the tape is at rest between incremental advances.

A power supply 50 in the form of a replaceable battery is connected with the various circuits through an interface circuit 52 connected with bus 40. The power supply provides power to the respective circuits of the system under the control of the microprocessor 32. The microprocessor 32 functions to control circuit operation and to process signals. The microprocessor also functions to enable digital signals which are to be recorded to be supplied to the tape head 45 while the tape is at rest.

Memory circuitry associated with the microprocessor is provided for storing information. In various applications, the memory circuit may include the integral memory of the microprocessor 32 as well as an external memory such as a buffer memory or a Random Access Memory, RAM, 35. In certain applications, the integral memory of the microprocessor 32 may provide sufficient memory capacity without requiring a separate external memory.

The microprocessor may receive its program instructions from an integral Read Only Memory, or ROM. Alternatively, a separate ROM 60 may be provided to supply the necessary program or operating instructions to microprocessor 32. The use of a separate ROM 60 may be desirable to permit substitution of separate ROM chips to provide different operating programs so as to enable the system to monitor different selected conditions of the subject. The program stored in the ROM 60 provides power control means associated with the microprocessor for continuously optimizing power usage of the system during subject monitoring. The power control means selectively prevents power from being respectively supplied to any selected circuit of the system at those time periods during monitoring when any such selected circuit is not required by the processor to perform functions requiring power usage. In addition, the power control means enables power to be respectively supplied to any selected circuit of the system only at those respective time periods during monitoring when any such selected circuit is required by the processor to perform a desired function requiring power usage and then only for the general time period required for any such selected circuit to perform the desired function.

Interface circuitry 52, for example, may contain the necessary circuitry to provide the tape-incrementing drive pulses, the power signals to the sensors 30, the power to appropriate current and/or voltage regulators as well as power-up and power-down switches for selected circuits of the system under the control of the microprocessor. Basically, all circuits requiring driving energy may receive such energy through interface circuitry 52 under the control of the microprocessor.

Figure 1:
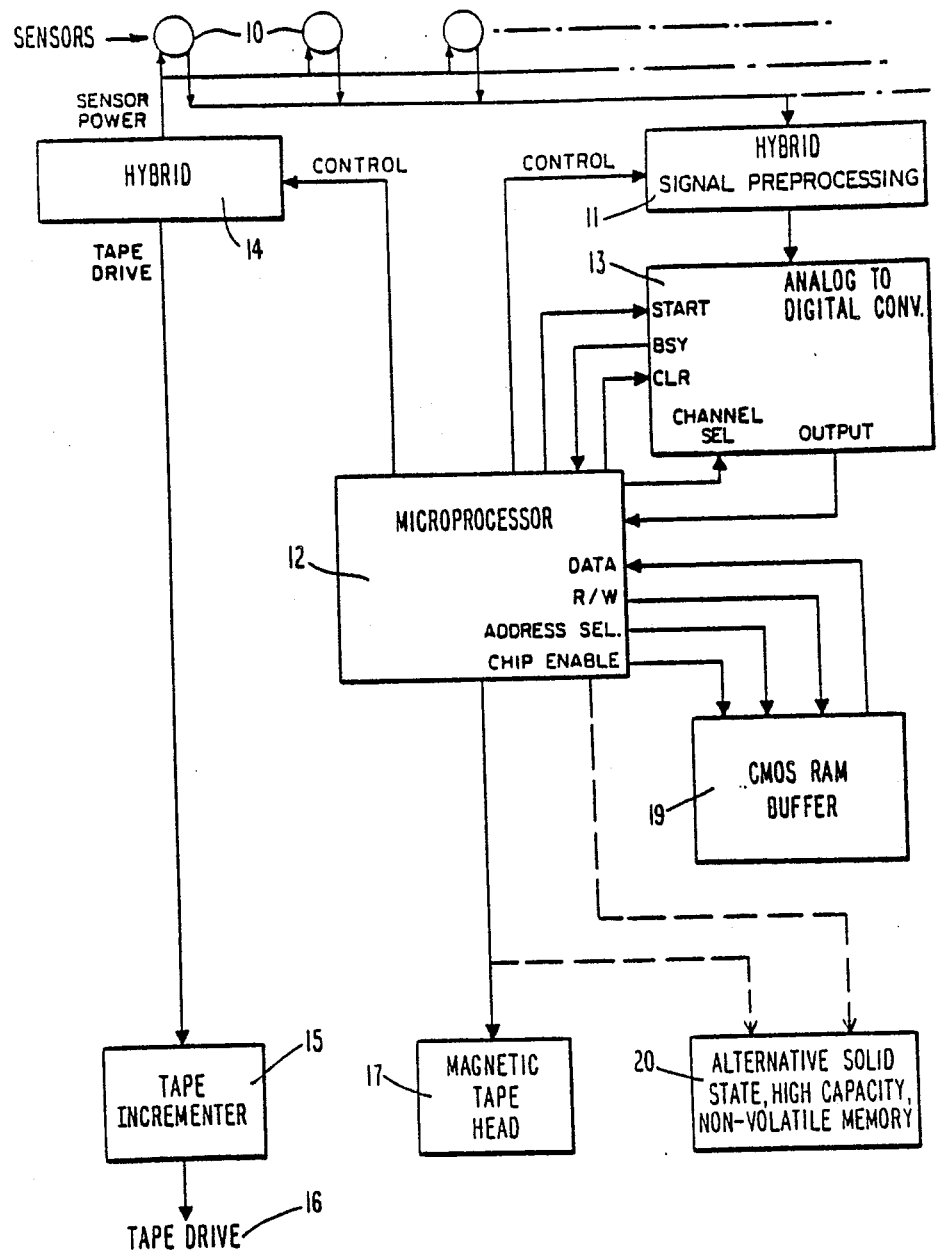
FIG. 1 is a functional block diagram showing the processing elements of the present invention.

In FIG. 1 of the drawings a more specific circuit arrangement in accordance with the present invention is depicted. A plurality of sensors 10 are shown which provide analog signals to signal preprocessing hybrid circuit 11 which operates under the control of microprocessor 12 to process the signals coming from sensors 10 to a form suitable for further processing to digital form by analog-to-digital converter 13. The output of converter 13 is in digital form and is fed to microprocessor 12 in this form. Microprocessor 12 has two control outputs, one of these controls hybrid circuit 11 and the other controls hybrid circuit 14. The output of hybrid circuit 14 controls tape incrementer 15 which in turn controls the intermittent advance of tape drive 16. The microprocessor 12 also feeds signals to the magnetic tape head 17 at times when the tape is at rest. A buffer 19 is provided to store in random access memory any data which exceeds the capacity of microprocessor 12. Such stored data is accessible by the microprocessor 12 for further processing. Alternative solid state, high capacity, nonvolatile memory is illustrated at unit 20.

Hybrid circuit 14 contains, in a microminiature configuration, the chips and thick-film circuitry to provide the tape-incrementing drive pulse, appropriate regulators (voltage and/or current), power-down and power-up switches—all controlled by the microprocessor 12. Basically, all sensors requiring driving energy receive that energy via this hybrid block 14.

Hybrid circuit 11 contains, in a microminiature configuration, the chips and thick-film circuits to pre-process sensed data coming from sensors 10. The preprocessed data is then fed to the Analog-to-Digital converter 13. Control of the hybrid unit 11 is maintained by the microprocessor 12.

Analog-to-Digital Converter 13 converts sensed and pre-processed analog data to digital data. While the conversion accuracy obtainable in an 8-bit system is preferred, the system is not limited to this number of significant bits. ADCs for 16, 32, etc. bits can be used by the system should a specific application make enhanced conversion accuracy desirable. Likewise, a 4-bit system is satisfactory for some cases. Converter unit 13 is controlled by the microprocessor 12. A suitable analog-to-digital converter unit may be the DATEL,DAS 952R made and sold by Datel-Intersil, Inc., Mansfield, Maine.

Microprocessor 12 provides essential control signals for the operation of the system via its internally programmed ROM. It controls sensor operational intervals, sequencing, selective power-down and power-up of the sensors and other circuits to conserve power, sense limit controls, function of the sensor-signal preprocessing circuitry, function of the on-board buffer memory 19, function of the converter 13, control of power regulators and on-off switches, tape incrementing control and tape-write signals to the recording head. It also performs such computational and timing functions as may be required of sensed data such as rates, sensed time intervals and maintenance of time and date data. Additionally, this unit will control a system of adaptive-delta-pulse-code-modulation (ADPCM) to optimize utilization of on-board memory. A typical unit may be the FUJITSU MB8851L made and sold by Fujitsu Microelectronics, Inc., Santa Clara, Calif.

Buffer memory 19 is required for storage of data sensed in a volume too large for immediate writing to the tape head 17 from microprocessor 12. When dealing with data such as cardiac arryhthmias, a substantial number of digitized samples of analog signal information is required. A typical record of such an episodic event may, for example, include the normal ECG-complex just prior to the arryhthmic beat, R—R interval spacing between the normal beat and the arryhthmic beat, the arryhthmic beat ECG-complex, and the time and date of occurrence. Once stored in buffer 19, such data will be appropriately read onto the tape through tape head 17 and the memory 19 will be cleared by microprocessor 12. A typical buffer unit may be the HARRIS, HM6514 made and sold by Harris Semiconductor, Melbourne, Fla.

Tape intermittent movement is based on incrementing the tape 18 by accurately controlled actuation of a capstan drive. In a preferred embodiment of the system a packing factor of about 4700 bits per inch per track may be achieved. As a result, the tape must be incremented 0.0002128 inches between records and this can be accomplished in a number of ways. It is important, however, to maintain very low power requirements to increment the tape. Since a full microcassette may require up to 8 million incremental steps, the power requirement per step is critically important. It is essential that the total system, including the power supply, be as small and light as possible, particularly when being worn by ambulatory human subjects for long periods of time. For this reason battery weight and size must be constrained which means that the power requirements must be very low. A miniature electromagnetic relay mechanism typically pulls an armature to an actuating coil core when the coil is energized. A sample relay unit required 2.9 v at 28 ma (pulsed for 20 ms) to provide an armature motion of 0.015 inches. Eight million such operations would require 1.24 amp-hrs of battery energy. The armature motion can be converted to appropriate capstan rotation by linking the armature to a pawl which incrementally rotates a detented ratchet gear one step for each armature activation. The ratchet gear is appropriately ratioed down so that the desired amount of linear tape motion is achieved and achieved very accurately.

A related variation to the foregoing would utilize a high efficiency electromagnetic circuit to drive the pawl and ratchet gear which in turn would rotate a worm linked to a miniature antibacklashed worm gear. By these means battery energy requirements may be reduced by about 50%. Since the magnetic circuits of sub-miniature relays generally sacrifice efficiency in available force for reasons of economy and size, this second approach has advantages over the use of a standard miniature relay as the source of the incremental tape motion driving force.

Other prime driving sources for tape incrementing, while not the preferred embodiment of our illustrated design, may include piezoelectric bender crystals and magnetostrictive elements. It should be noted that the use of commercially available stepping motors or controlled rotating motors requires excessive battery energy and therefore such devices are not preferred for the present invention at this time.

In the preferred embodiment of the invention a microcassette magnetic tape and a non-digital audio 4-track recording head are used. (Brush Magnetic Heads, Division of Forgflo Corporation, Sunbury, Pa.). However, the same system is operable using other combinations such as an 8-track head with $\frac{1}{4}$ inch tape.

Figure 2:
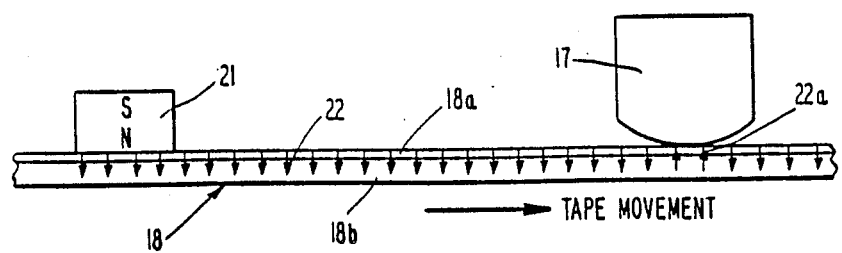
FIG. 2 is a diagrammatic showing of the tape and associated prepolarizer and tape recording head.

FIG. 2 of the drawings shows, in diagrammatic form, a prepolarization magnet 21, and a recording tape 18 and its associated oxide layer 18a. Prepolarization of the oxide layer 18a on support web 18b of the tape is carried out as the tape passes under magnet 21, and is indicated by reverse arrows 22. Recording is carried out by pulses from a non-digital audio recording head 17 which acts to cause a reverse polarization at the oxide layer 18a of the tape 18, as indicated by the direction of the arrows 22a located directly under the central part of the recording head 17.

Figure 3:
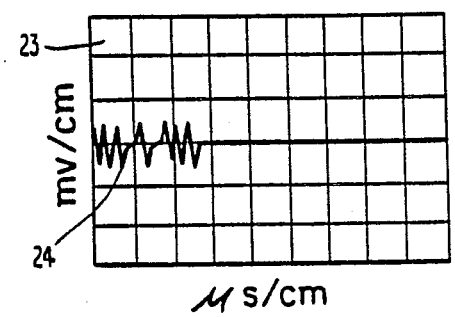
FIG. 3 is a showing of a wave form taken directly from one of the tape head tracks.

In FIG. 3 there is shown an analog waveform as it appears on the screen 23 of an oscilloscope connected to one of the playback tracks of recording head 17. The playback frequency for this analog waveform 24 was 26.3 KHz, which was found to be a very satisfactory playback frequency for use in the practice of the present invention.

Figure 4:
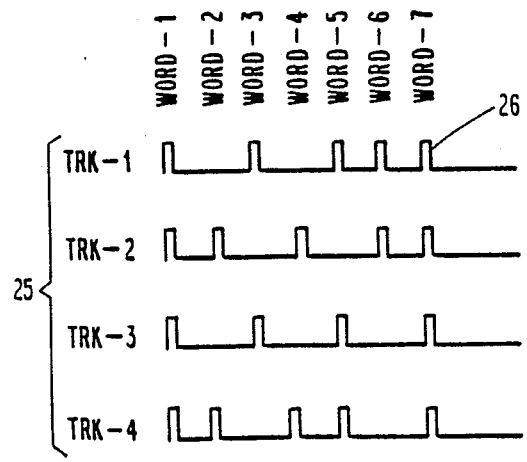
FIG. 4 is a showing of the wave form output amplified and squared from a four track tape head.

FIG. 4 is a reproduction of an oscilloscope display illustrating seven 4-bit words. These 4-bit words are made up of pulses obtained by amplifying and squaring the analog waveforms present at each of the four tracks 25 at tape head 17. An optimum tape pulse packing factor is 4700 bpi per track. In FIG. 4 word-1 is 1,1,1,1; word-2 is 0,1,0,1; word-3 is 1,0,1,0 and so on for the remainder of the seven words. In the practice of the present invention other word lengths may be used. However, the preferred word length for use in the practice of the present invention is 8 bits.

Power usage, and particularly the optimization of power usage during the monitoring process, is carefully controlled by the system in order to extend the time period of monitoring without unnecessary interruption caused by the need for replacement of batteries. The system minimizes power consumption by providing a relatively high packing factor of information on the recording tape even though a standard non-digital audio recording head is utilized. The use of a standard non-digital audio recording head provides significant cost savings over the use of a digital recording head. However, by carefully controlling the recording pulses used to reverse the polarization of prepolarized recording tape, a relatively high packing factor of information on the recording tape can still be achieved. The maximum packing factor, or in other words, the minimum spacing between bits of information recorded on tape is approximately three times the gap width of the recording head. For example, if a standard four track recording head having a gap width of $65 \times 10^{-6}$ inches is utilized, polarization reversals representing bits of information may be spaced at intervals of approximately $195 \times 10^{-6}$ inches. Accordingly, a maximum of about 5128 bits may be recorded on each recording track of the tape per inch of tape. In order to provide a safe error margin, an optimum packing factor of about 4700 bits per inch per track of tape may be used to provide a spacing of about $212.8 \times 10^{-6}$ inches between bits of information. This computes to a spacing between bits of information of about 3.3 times the gap width of the recording head. Accordingly, a 90-minute standard microcassette tape containing 2551 inches of tape will have the capacity for recording on four tracks approximately $47.96 \times 10^{-6}$ bits, or approximately 6 megabytes, of information.

An optimum write pulse for driving the four-track recording heads simultaneously may be a pulse generally approximating a square wave of approximately $150 \times 10^{-6}$ seconds duration with a magnitude of the voltage of the pulse dropping from 0.35 volts to 0.25 volts during the duration of the pulse and the amplitude of the current increasing from $3.25 \times 10^{-3}$ amps to approximately $4.10 \times 10^{-3}$ amps during the duration of the pulse. For recording on the four tracks, the average peak current would therefore be approximately $3.7 \times 10^{-3}$ amps which would result in an average peak power for the four heads of approximately $1.23 \times 10^{-3}$ watts. Accordingly, if a bit is recorded in every position on the standard 90-minute recording tape, the total power consumption for writing or recording approximately $47.96 \times 10^6$ bits of information would be about 2.25 watts. An average power consumption for the four tracks would be approximately $0.187 \times 10^6$ watts with a resulting average power per bit of approximately $4.692 \times 10^{-8}$ watts. A total current-time requirement for recording is approximately 1.85 mA-hours. However, if an efficiency of the write pulse of approximately 50% is assumed, the total current-time requirement would be approximately 3.7 mA-hours, which is a current-time requirement that is smaller than the capability of some of the smallest hearing aid batteries presently available.

Power usage is also effectively optimized by carefully controlling the application of power to the various circuits of the system. The microprocessor is programmed via an internal ROM or an external ROM to selectively power down various circuits of the system at any time during the monitoring process that such circuits are not required to perform active operations requiring power consumption.

Power control of selected circuits of the system during monitoring can be exemplified by several specific applications of the system. For the detection of the panic syndrome, the system must monitor heart rate and skin temperature. The microprocessor is programmed to detect panic syndrome when for example, the detected heart rate is greater than 100 beats per minute and the detected skin temperature is simultaneously less than 97° F. Because of the latency in such physiological parameters, however, the sensing of the heart rate and the skin temperature can occur, for example, only once every ten seconds. The time period of ten seconds is selected merely as an example, since clinical data may reveal that a sensing period of up to 60 seconds or even longer may still be effective. If the internal memory of the microprocessor is sufficient to temporarily store information relating to the sensed data, an external buffer memory is not required. As a result, the buffer memory in the system may be powered down during the entire monitoring process. Since the actual sensing of the requisite data may be completed in approximately one second, all circuits in the system except for the microprocessor may be powered down for the remaining nine-second interval during each ten second period. During the one-second time interval when sensing occurs, the necessary sensors for skin temperature and heart rate, as well as the related interface circuits including the preprocessing circuit, are powered up. After being sensed, the ECG signal is then analyzed either as an analog signal in the preprocessing circuit or alternatively by the processor to determine the R—R interval. If the R—R interval is determined to be less than 0.6 seconds and the skin temperature is simultaneously less than 97° F., then the tape drive circuits are powered up to permit recording of the essential data. The microprocessor will also cause the time and date of the episode to be recorded on the tape via the tape head with the tape being incremented as required under the control of the microprocessor. In applications where both the temperature and the R—R interval are analyzed in analog form in the preprocessing circuit to determine the occurrence of an episode, the microprocessor will, upon detection of an episode, power up the analog-to-digital circuit. The microprocessor will then cause the temperature signal and/or the R—R interval data to be digitized by the powered-up analog-to-digital circuit and will thereafter cause the resulting digital signal to be recorded on the recording tape. After the information is recorded, the analog-to-digital converter circuit and the tape drive circuit are then powered down. If, for example, only the temperature signal is required to be digitized by the analog-to-digital converter, the converter can be powered down immediately following the conversion of the temperature signal into digital format. Thereafter, data representing the R—R interval can be supplied in digital form from the preprocessing circuit via the microprocessor to the recording head and then the tape drive circuit can be powered down. In the next ten-second period, if the temperature is once again less than 97° F. and the heart rate is simultaneously greater than 100 beats per minute, the necessary recording of information will repeat. If, however, the temperature is greater than 97° F., and/or the heart rate is less than 100 beats per minute, all circuits except for the microprocessor can remain quiescent for another ten second time period until the temperature and heart beat are once again sensed.

Another example in which various circuits of the system may be powered-up and powered-down as required during monitoring in order to conserve power is the simple detection of bradycardia or tachycardia. The system monitors the subject for the occurrence of bradycardia or tachyicardia as determined by preset limits. For example, bradycardia will occur if the heart rate is less than 60 beats per minutes and the R—R interval is greater than one second, and tachycardia will occur if the heart rate is greater than 110 beats per minute and the R—R interval is less than 0.545 seconds. If either preset limit is exceeded, then the date and time of the episode and the R—R interval will be recorded. In this situation, the buffer memory and an analog-to-digital converter circuit may not be required so these circuits may be powered down for the entire monitoring process. During monitoring, the microprocessor and the signal preprocessing circuits are powered up. Upon detecting that either preset limit is exceeded, the microprocessor in cooperation with the signal preprocessing circuit will establish a value in milliseconds for the R—R interval. The microprocessor will then power up the tape drive circuit so that the date and time of the occurrence as well as the R—R interval can be recorded on the recording tape with the tape being incremented as required under microprocessor control. The tape drive circuits will then be powered down as the system continues to monitor the patient. In this particular application, a subject utilizing the system of the present invention can be maintained under continuous surveillance for an estimated 18-36 weeks.

Another example in which selected circuits of the system are powered up and powered down to conserve power usage involves the detection of simple arrhythmias. In this application, the heart rate based on the sensed R—R interval is continuously averaged over five R—R intervals. Every 15 minutes, the average heart rate will be recorded on the tape. For this purpose, the microprocessor and signal preprocessing circuits will be powered up during monitoring to permit the continuous averaging of the heart rate. As the system continues to monitor and generate average R—R intervals, the tape drive circuits will be powered up briefly every 15 minutes so that the microprocessor can enable the average R—R interval at that time period to be recorded on the tape. The tape will be incremented as necessary under the control of the microprocessor and after recording of the data at the 15 minute interval has been completed, the tape drive circuits will be powered down. If a presently sensed R—R interval differs from the average R—R interval by a predetermined amount, then the R—R interval will be considered to be representative of an arrhythmic episode and the occurrence will be recorded on the tape. The tape drive circuits will be powered up so that the microprocessor will enable selected information reflecting the arrhythmic, for example, the date and time of the occurrence and the duration of the arrhythmic R—R interval to be recorded on the tape. Depending on the type and amount of additional information to be recorded, the buffer memory and/or the analog-to-digital circuit may not be required and, therefore, such circuits may be powered down if not needed during the monitoring process. Once again, necessary tape incrementing will occur under microprocessor control and the tape drive circuits will be powered down once the recording has been completed.

In certain applications it will be necessary to accept and record in digital format complex analog data such as the electrocardiographic (ECG) signal. For example, in the monitoring and recording of the cardiac arrythmia episodes, it may be desirable for purpose of analysis to record the last normal ECG waveform, the R—R interval to the ectopic beat, the ectopic beat itself, the time of occurrence, as well as other information. If the system is programmed to record only the abnormality when it occurs, each ECG will be sensed, standardized, and converted to digital form and temporarily stored in the buffer memory. If each successive ECG pulse is normal, the previous ECG pulse stored in memory will be deleted from the memory and the new pulse will be memorized. If any successive pulse or pulses are abnormal, then both the last normal ECG pulse and the successive abnormal pulse or pulses of interest will be recorded onto tape and the buffer will be cleared of such data. While subject monitoring takes place in real time, the recording of pertinent data on tape occurs at a later time. However, since the time and date of the episode is recorded with the desired ECG pulses, the relationship of the data to real time is not lost. In this type of application requiring the use of an external buffer memory, the memory circuit will be powered up only when the storage capacity required exceeds the available memory of the microprocessor. As quickly as possible, consistent with the logical requirements for data and recording sequences, the buffer memory will be completely powered down once it is no longer needed and will remain powered down until it is again needed.

In different applications, other circuits may also be powered up and powered down as needed. For example, in applications requiring the use of powered sensors in which continuous sensing is not necessary, the sensor circuits will be powered down except when a reading is required.

As a general matter, various selected circuits of the system will be powered up and powered down based on the logic of the problem being handled. The logical control of supplying and removing power from various circuits is significant in the conservation of available energy from the battery. The logical control of power greatly extends the operational lifetime of the system between battery replacements. Of course, many variations will be possible with the system, depending on the capability of the microprocessor and the particular ROM selected. By providing a system which will accept, for example, replacement ROMs or microprocessors or modification circuits for different applications to enable the system to monitor different selected conditions, system flexibility will be greatly enhanced.

From the above description of the present invention it will be noted that it is essential that a capability for extended periods of use such as weeks, months or even years be provided. Likewise, the total weight of the system, including its power supply must be minimal, such as on the order of less than 8 ounces, particularly for use on ambulatory human subjects. To accomplish these objectives the system operates on a power supply which supplies full power only at particular times and the average power used is in the micropower range. Since the system is substantially powered down most of the time, the power requirements are substantially less than conventional systems. Moreover, the power required for advancing the magnetic tape and the time during which such power is supplied are at a minimum since the tape advance is incremental and the advance mechanism draws very little total current during the short time it operates.

What is claimed is:

1. A portable data acquisition and recording system capable of being carried on an ambulatory subject for monitoring selected conditions of the subject over a selected time period having a recording tape and power supply, the system comprising:

(a) sensor means in communication with the subject for sensing at least one selected parameter of the subject and having a sensor circuit for producing signals representing the parameter being sensed;

(b) an interface circuit connected with the sensor circuit for converting the signals originating at the sensor circuit into digital signals of a selected format;

(c) a recording head for recording digital signals on said recording tape in a limited area adjacent said recording head;

(d) tape drive means having a tape drive circuit for advancing the tape to permit recording of successive digital signals on said tape;

(e) a microprocessor for controlling system circuit operation, for processing signals and for enabling digital signals to be supplied to the recording head for recording onto the tape; and (f) power control means associated with the system for continuously optimizing power usage of the system during subject monitoring, the power control means being connected to said circuits and energizing said sensor circuit to produce signals, and, in response to the signals produced by said sensor circuit, selectively preventing power from energizing any selected circuit of the system at time periods during monitoring when any such selected circuit is not required by said signals to perform functions requiring power usage and selectively enabling power to energize any selected circuit of the system at time periods during monitoring when any such selected circuit is required by said signals to perform a desired function requiring power usage.

2. The system in accordance with claim 1 wherein the interface circuit includes:

(a) a signal preprocessing circuit connected with the sensor circuit for modifying signals originating at the sensor circuit; and (b) an analog-to-digital converter circuit connected with the signal preprocessing circuit for converting analog signals from the signal preprocessing circuit into digital signals.

3. The system in accordance with claim 2 wherein the power control means selectively enables power to energize said analog-to-digital converter circuit at said time periods during monitoring when power is required in response to the parameter being sensed.

4. The system in accordance with claim 2 wherein the power control means selectively enables power to energized said signal preprocessing circuit at said time periods during monitoring when power is required in response to the parameter being sensed.

5. The system in accordance with claim 1 wherein the power control means selectively enables power to energize at least one of said selected circuits of the system at said time periods during monitoring when power is required in response to the parameter being sensed.

6. The system in accordance with claim 1 comprising a memory circuit associated with the microprocessor for storing information and wherein said memory circuit includes an integral memory of the microprocessor.

7. The system in accordance with claim 1 comprising a memory circuit associated with the microprocessor for storing information and wherein the memory circuit includes a buffer memory circuit separate from the microprocessor.

8. The system in accordance with claim 7 wherein the power control means selectively enables power to energize said buffer memory circuit of the system at time periods during monitoring when power is required in response to the parameter being sensed.

9. The system in accordance with claim 1 wherein said tape drive circuit comprises an incremental tape drive circuit for incrementally advancing the tape to permit recording of successive digital signals on said tape while the tape is at rest between incremental advances.

10. The system in accordance with claim 9 wherein the recording head is an audio recording head and wherein the microprocessor controls the form of the digital signals supplied to the recording head to enable a total average power consumption for writing bits of digital information on the tape of less than $4.692 \times 10^{-8}$ watts per bit of information.

11. The system in accordance with claim 9 wherein said recording tape is prepolarized and said recording head records digital signals by intermittently reversing the tape polarization while the tape is at rest in response to the digital signals supplied to the recording head.

12. The system in accordance with claim 11 comprising a prepolarizing circuit for prepolarizing the recording tape.

13. The system in accordance with claim 1 wherein the system includes at least one replacement circuit which is interchangeable with a selected circuit of the system to enable the system to monitor different selected conditions of the subject.

14. The system in accordance with claim 13 comprising a ROM circuit separate from the microprocessor for providing program instruction to the microprocessor and wherein said system includes a replacement ROM circuit.

15. The system in accordance with claim 1 wherein the power control means selectively enables power to energize said sensor circuit at said time periods during monitoring when power is required.

16. The system in accordance with claim 1 wherein the power control means selectively enables power to energize said tape drive circuit at said time periods during monitoring when power is required in response to the parameter being sensed.

17. The system in accordance with claim 1 wherein the system includes at least one modification circuit insertable into the system to enable the system to monitor different selected conditions of the subject.

18. A portable data acquisition and recording system having a power supply and a recording medium for monitoring selected parameters of a subject over a prolonged time period, the system comprising:
(a) sensor means in communication with the subject for sensing at least one selected parameter of the subject and having a sensor circuit for producing successive signals representing the parameter being sensed;
(b) an interface circuit connected with the sensor circuit for converting the signals originating at the sensor circuit into digital signals;
(c) a recording head for recording said digital signals on said recording medium;
(d) medium drive means having a medium drive circuit for advancing the medium to permit recording of said digital signals on said medium;
(e) a microprocessor for controlling system circuit operation, for processing signals and for enabling digital signals to be supplied to the recording head for recording onto the medium; and
(f) power control means connecting said power supply to the circuits of the system and energizing the sensor circuit to produce signals, said power control means continuously optimizing power usage of the system during monitoring, and in response to the signals produced by said sensor circuit, selectively preventing energization of any selected circuit of the system at time periods during monitoring when such selected circuit is not required by said signals to perform functions and selectively energizing any selected circuit of the system at time periods during monitoring when such selected circuit is required by said signals to perform a desired function requiring power.

19. The system according to claim 18 wherein each of said selected circuits has individual power-up connections to said power control means, said power-up connection being activated only in response to predetermined signals produced by said sensor means.

20. The system according to claim 18 for monitoring a combination of parameters wherein said microprocessor includes means establishing a normal condition from the combination of said sensed parameters, said power control means being operable, upon occurrence of an abnormal condition resulting in deviation of said sensed parameters from said established normal condition, to supply signals to said recording head and to energize said medium drive circuit to effect a recording on said medium, whereby said medium drive circuit is supplied with power and recordings are effected only upon occurrence of an abnormal condition.

21. A portable data acquisition and recording system capable of being carried on an ambulatory subject for monitoring selected conditions of the subject over a selected time period having a recording tape and power supply, the system comprising:
(a) sensor means in communication with the subject for sensing at least one selected parameter of the subject and having a sensor circuit for producing signals representing the parameter being sensed;
(b) an interface circuit connected with the sensor circuit for converting the signals originating at the sensor circuit into digital signals of a selected format;
(c) a recording head for recording digital signals on said recording tape in a limited area adjacent said recording head;
(d) tape drive means having a tape drive circuit for advancing the tape to permit recording of successive digital signals on said tape, said tape drive circuit including an incremental tape drive circuit for incrementally advancing the tape to permit recording of successive digital signals on said tape while the tape is at rest between incremental advances;
(e) a microprocessor for controlling system circuit operation, for processing signals and for enabling digital signals to be supplied to the recording head for recording onto the tape; and
(f) power control means associated with the system for continuously optimizing power usage of the system during subject monitoring, the power control means selectively preventing power from energizing any selected circuit of the system at time periods during monitoring when any such selected circuit is not required to perform functions requiring power usage and selectively enabling power to energize any selected circuit of the system at time periods during monitoring when any such selected circuit is required to perform a desired function requiring power usage.

22. The system in accordance with claim 21 wherein the recording head is an audio recording head and wherein the microprocessor controls the form of the digital signals supplied to the recording head to enable a total average power consumption for writing bits of digital information on the tape of less than $4.692 \times 10^{-8}$ watts per bit of information.

23. The system in accordance with claim 21 wherein said recording tape is prepolarized and said recording head records digital signals by intermittently reversing the tape polarization while the tape is at rest in response to the digital signals supplied to the recording head.

24. The system in accordance with claim 23 comprising a prepolarizing circuit for prepolarizing the recording tape.

25. The system according to claim 21 wherein each of said circuits has individual power-up connections to said power control means, said power-up connection being activated only in response to predetermined signals produced by said sensor means.

26. The system according to claim 25 for monitoring a combination of parameters wherein said microprocessor includes means establishing a normal condition from the combination of said sensed parameters, said power control means being operable upon occurrence of an abnormal condition resulting in deviation of said sensed parameters from said established normal condition, to supply signals to said recording head and to energize said tape drive circuit to effect a recording on said recording tape, whereby said tape drive circuit is supplied with power and recordings are effected only upon occurrence of an abnormal condition.

* * * * *

UNITED STATES PATENT AND TRADEMARK OFFICE
CERTIFICATE OF CORRECTION

PATENT NO.   : 4,894,728
DATED        : January 16, 1990
INVENTOR(S)  : ROBERT M. GOODMAN It is certified that error appears in the above-identified patent and that said Letters Patent is hereby corrected as shown below:

Column 2, lines 50-51, "a periodic" should be --aperiodic--;

Column 8, line 21, "$47.96 \times 10^{-6}$" should be --$47.96 \times 10^{6}$--;

Column 8, line 40, "$0.187 \times 10^{6}$" should be --$0.187 \times 10^{-6}$--;

Column 10, line 43, "arrhythmic" should be --arrhythmia--;

Column 12, lines 46-47, "energized" should be --energize--.

Signed and Sealed this

Sixteenth Day of July, 1991

Attest:

HARRY F. MANBECK, JR.

*Attesting Officer*   *Commissioner of Patents and Trademarks*